DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED AUG. 1, 1972

901 O.G. 7

T901,006

PREPARATION OF DIALKYL XANTHOGEN DISULFIDES

Leo Ojakaar, Hockessin, Del., assignor to E. I. du Pont de Nemours and Company, Wilmington, Del.

Filed Apr. 23, 1971, Ser. No. 137,056
Int. Cl. C07c *154/02*
U.S. Cl. 260—455 B
No Drawing. 11 Pages Specification

According to this invention there is provided a process for preparing dialkyl xanthogen disulfides in good yield and high purity by contacting at a temperature in the range of about 15–30° C. a gas stream containing about 6–16% chlorine gas by volume, and an alkaline aqueous solution of an alkali metal salt of an alkyl xanthic acid and an alkyl in which the alkyl radical corresponds to that of the alkyl xanthic acid salt, the molar ratio of alcohol to xanthic acid salt being at least about 0.5:1 and the pH of the solution being about 10 or higher. The alkyl radicals in the alkyl xanthic acid have one to eight carbon atoms. The preferred molar proportions are 0.9 to 1.1 mole of alcohol per mole of xanthate.

Dialkyl xanthogen disulfides can be produced by a continuous two-step process, e.g. by (1) reacting the alcohol with carbon disulfide in the presence of an alkali metal hydroxide to produce the metal salt of the xanthic acid, then (2) oxidizing the metal salt of the xanthic acid with chlorine to the disulfide. Alternatively, the disulfide can be prepared as in step (2) using a xanthic acid metal salt produced by any one of several known methods. With the continuous two-step process, the excess alcohol necessary for the process of this invention can be present in step (1) or may be added by step (2).

The chlorine which is added in diluted form in a stream of an inert gas such as air or oxygen, should be introduced into the liquid reaction mixture below the surface to avoid local concentrations of chlorine.

By the process of this invention diethyl xanthogen disulfide having a freezing point of about 26° C. or higher can be produced in good yield.